US00PP31850P2

(12) United States Plant Patent
Hamilton et al.

(10) Patent No.: US PP31,850 P2
(45) Date of Patent: Jun. 9, 2020

(54) RASPBERRY PLANT NAMED 'DRISRASPFOURTEEN'

(50) Latin Name: ***Rubus idaeus* L.**
Varietal Denomination: DrisRaspFourteen

(71) Applicant: Driscoll's, Inc., Watsonville, CA (US)

(72) Inventors: Brian K. Hamilton, Watsonville, CA (US); Matthias D. Vitten, Watsonville, CA (US); Moises D. Gonzalez, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/350,839

(22) Filed: Jan. 22, 2019

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./203, 204
See application file for complete search history.

(56) References Cited

U.S. PATENT DOCUMENTS

| | | | |
|---|---|---|---|
| PP4,486 | P | 11/1979 | Reiter |
| PP6,493 | P | 12/1988 | Wilhelm |
| PP7,436 | P | 2/1991 | Ackerman |
| PP7,437 | P | 2/1991 | Ackerman |
| PP7,528 | P | 5/1991 | Ackerman |
| PP8,022 | P | 11/1992 | Wilhelm |
| PP8,027 | P | 11/1992 | Wilhelm |
| PP9,340 | P | 10/1995 | Wilhelm et al. |
| PP9,653 | P | 10/1996 | Wilhelm et al. |
| PP9,696 | P | 11/1996 | Fear |
| PP11,067 | P | 9/1999 | Fear et al. |
| PP11,087 | P | 10/1999 | Fear et al. |
| PP11,094 | P | 10/1999 | Fear et al. |
| PP11,102 | P | 10/1999 | Fear et al. |
| PP14,761 | P2 | 5/2004 | Fear et al. |
| PP14,781 | P2 | 5/2004 | Fear et al. |
| PP14,804 | P2 | 5/2004 | Fear et al. |
| PP14,860 | P2 | 6/2004 | Fear et al. |
| PP14,903 | P2 | 6/2004 | Fear et al. |
| PP14,904 | P2 | 6/2004 | Fear et al. |
| PP18,658 | P3 | 3/2008 | Fear et al. |
| PP18,659 | P3 | 3/2008 | Fear et al. |
| PP19,137 | P3 | 8/2008 | Harrison et al. |
| PP19,656 | P2 | 1/2009 | Hamilton et al. |
| PP22,246 | P3 | 11/2011 | Hamilton et al. |
| PP22,731 | P2 | 5/2012 | Fear et al. |
| PP23,477 | P3 | 3/2013 | Hamilton et al. |
| PP24,610 | P3 | 7/2014 | Hamilton et al. |
| PP25,044 | P3 | 11/2014 | Hamilton et al. |
| PP25,045 | P3 | 11/2014 | Hamilton et al. |
| PP27,644 | P3 | 2/2017 | Hamilton et al. |
| PP28,775 | P2 | 12/2017 | Hamilton et al. |
| PP28,856 | P3 | 1/2018 | Vitten et al. |
| PP29,402 | P2 | 6/2018 | Vitten et al. |

OTHER PUBLICATIONS

Cousineau et al., "Use of Isoenzyme Analysis to Characterize Raspberry Cultivars and Detect Cultivar Mislabeling", HortScience vol. 27, No. 9, Sep. 1992, pp. 1023-1025.
Hamilton et al., Unpublished U.S. Appl. No. 15/932,178, filed Feb. 15, 2018, titled "Raspberry Plant Variety Named 'DrisRaspEleven'".
Vitten et al., Unpublished U.S. Appl. No. 15/732,501, filed Nov. 20, 2017, titled "Raspberry Plant Named 'DrisRaspTwelve'".
Williams et al., "DNA Polymorphisms Amplified by Arbitrary Primers are useful as Genetic Markers", Nucleic Acids Research, vol. 18, No. 22, 1990, pp. 6531-6535.

*Primary Examiner* — Susan McCormick Ewoldt
(74) *Attorney, Agent, or Firm* — Morrison & Foerster LLP

(57) ABSTRACT

A new and distinct variety of raspberry plant named 'DrisRaspFourteen', particularly selected for its primocane and floricane yield, fruit size, and fruit flavor, is disclosed.

4 Drawing Sheets

Latin name:
Botanical classification: *Rubus idaeus* L.
Varietal denomination: The varietal denomination of the claimed variety of raspberry plant is 'DrisRaspFourteen'.

BACKGROUND OF THE INVENTION

Raspberries are the edible fruit of a multitude of plant species in the genus *Rubus* of the rose family. Most raspberry species are in the subgenus Idaeobatus. Raspberry plants are perennial plants with woody stems. Many of the most important modern commercial red raspberry cultivars derive from hybrids between *R. idaeus* and *R. strigosus*. Recent breeding has resulted in cultivars that are thornless and more strongly upright, not needing staking.

Both the red and the black raspberry species have albino-like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warm climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purées, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

In order to meet these needs, the present invention is directed to an improved variety of raspberry plant. In particular, the invention relates to a new and distinct variety of raspberry plant (*Rubus idaeus* L.), which has been denominated as 'DrisRaspFourteen'.

Raspberry plant named 'DrisRaspFourteen' was discovered in Ventura County, Calif. in March of 2011 and originated from a cross between the proprietary female parent raspberry variety 'RB629.4' (unpatented) and the proprietary male parent raspberry variety 'Y454.3' (unpatented). The original seedling of the new variety was first asexually propagated. via cuttings in Ventura County, Calif. in May of 2011.

'DrisRaspfourteen' was subsequently asexually propagated via root cuttings, and underwent further testing in Ventura County, Calif. for nine years (2010 to 2018). The present variety has been found to be stable and reproduce true to type through successive asexual propagations via root cuttings in Ventura County, Calif.

'DrisRaspFourteen' exhibits the following distinguishing characteristics over similar raspberry varieties when grown under normal horticultural practices in Ventura County, Calif.:

1. Sparse spines on canes;
2. Convex profile of leaflets in cross section; and
3. Anthocyanin coloration present on peduncle.

'DrisRaspFourteen' was particularly selected for its primocane and floricane yield, fruit size, and fruit flavor.

BRIEF DESCRIPTION OF THE DRAWINGS

This new raspberry plant is illustrated by the accompanying photographs. The colors shown are as true as can be reasonably obtained by conventional photographic procedures. The photographs are of plants that are from one to two years old.

DETAILED BOTANICAL DESCRIPTION

Figure 1:
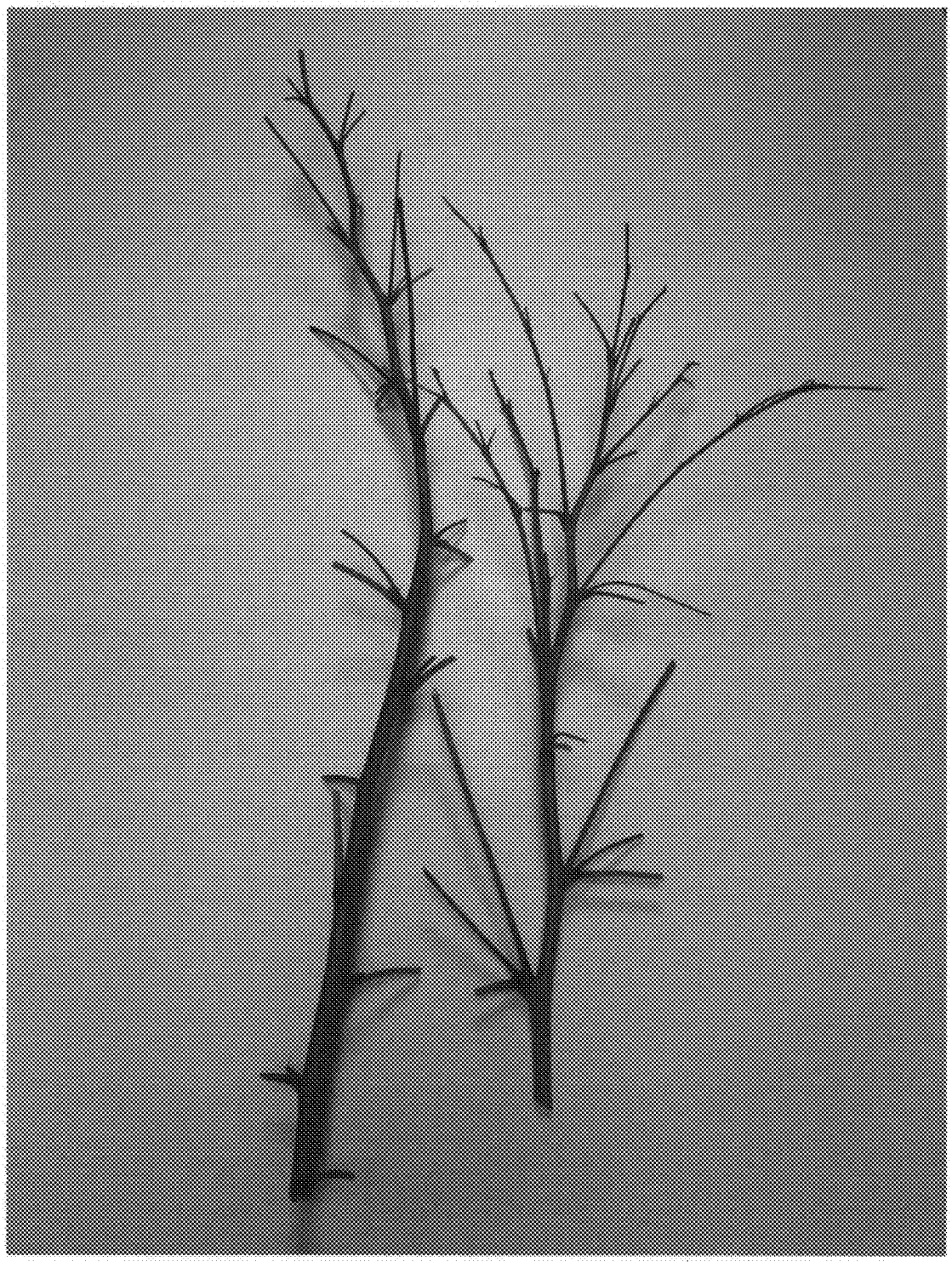
FIG. 1 illustrates sections of canes of raspberry variety 'DrisRaspFourteen'.
Figures 2A, 2B:
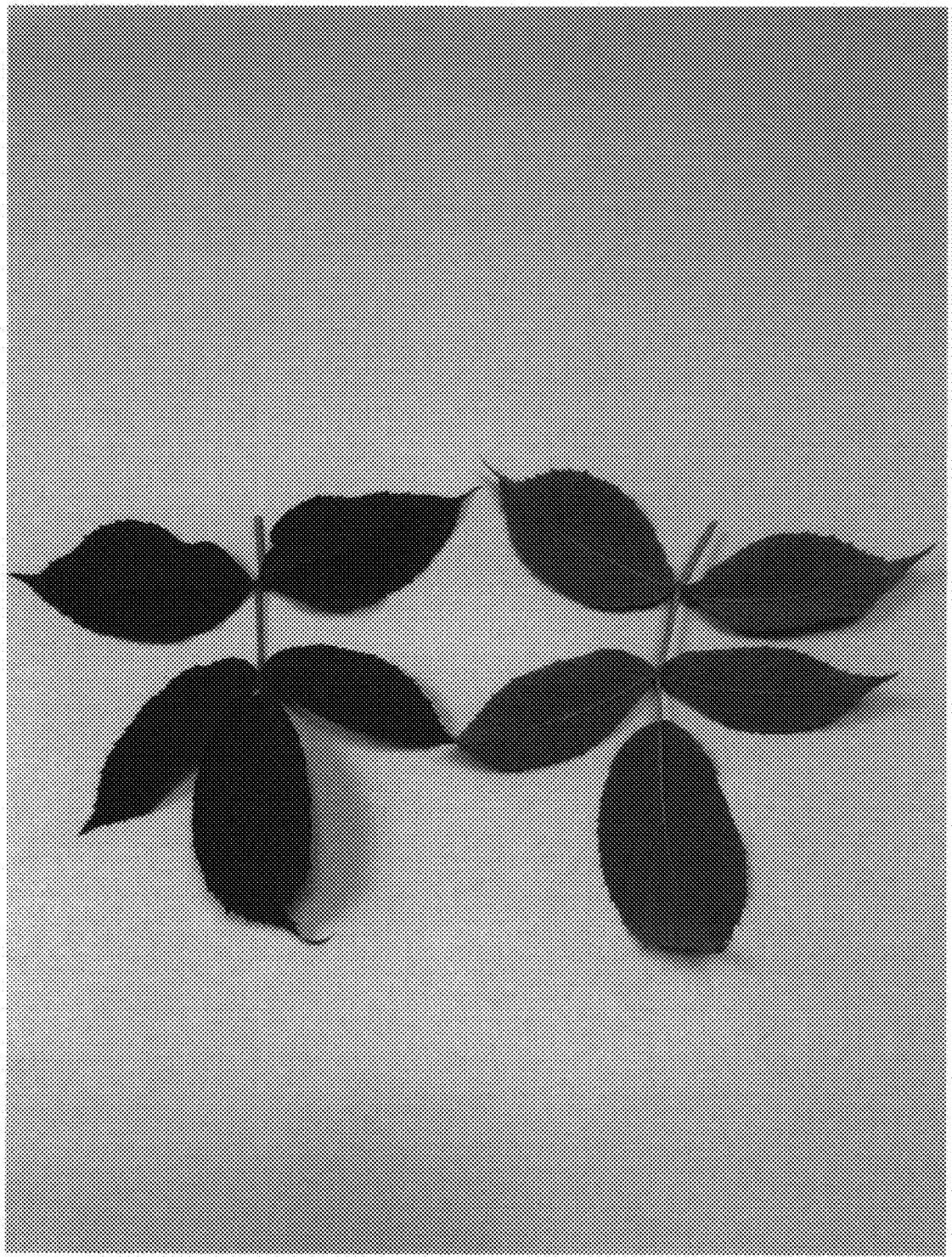
FIG. 2A and FIG. 2B illustrate both the upper surface (FIG. 2A) and the lower surface (FIG. 2B) of leaves of raspberry variety 'DrisRaspFourteen'.
Figure 3:
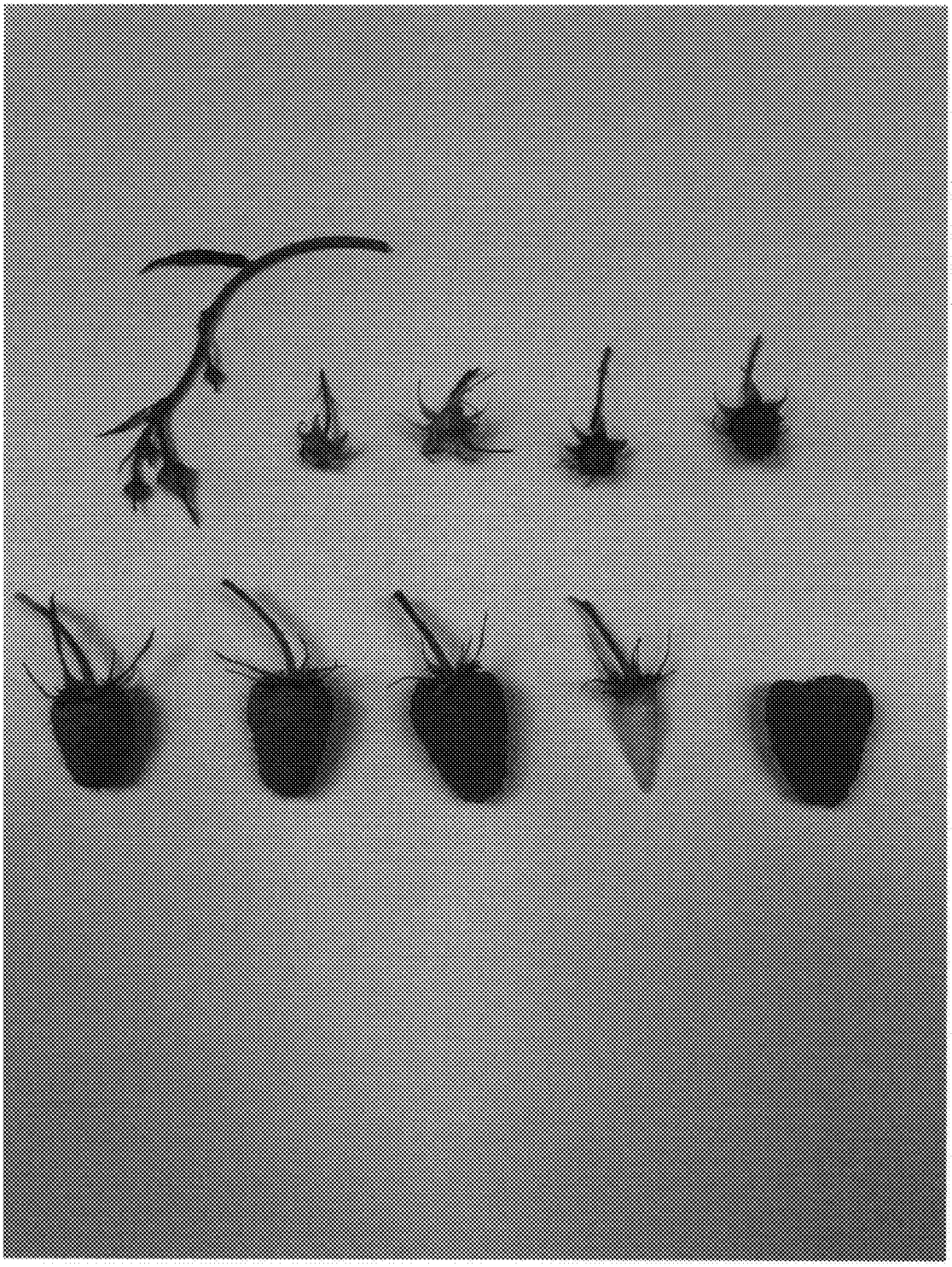
FIG. 3 illustrates fruit of raspberry variety 'DrisRaspFourteen' at various stages of development.
Figure 4:
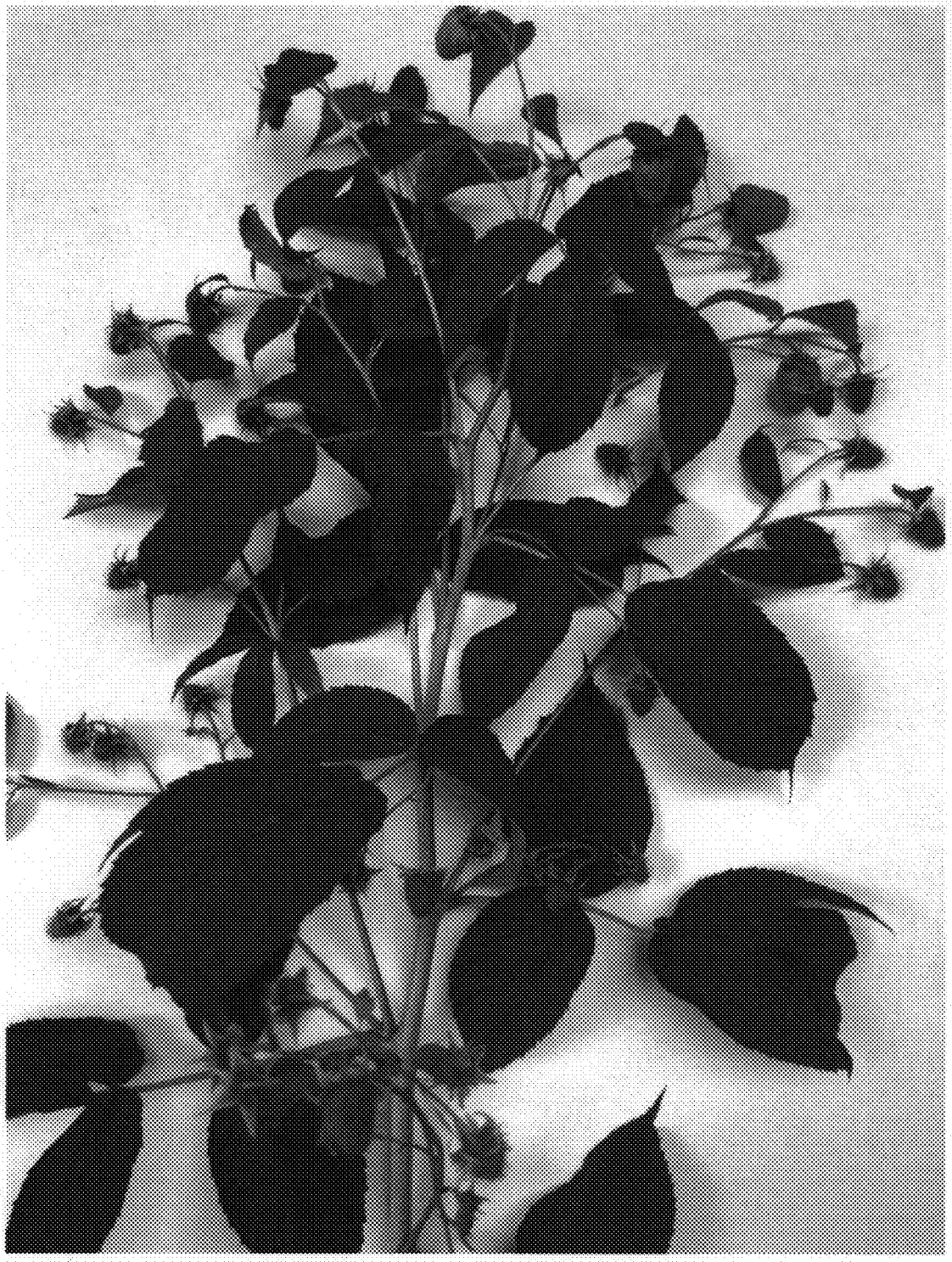
FIG. 4 illustrates plants of raspberry variety 'DrisRaspFourteen'.

The following descriptions set forth the distinctive characteristics of 'DrisRaspFourteen'. Unless where otherwise noted, the data that define these characteristics are based on observations taken from 'DrisRaspFourteen' plants that were one to two years old, grown in Ventura County, Calif. from 2010 to 2018. These descriptions are in accordance with UPOV terminology. Color designations, color descriptions, and other phenotypical descriptions may deviate from the stated values and descriptions depending upon variation in environmental, seasonal, climatic and cultural conditions. 'DrisRaspFourteen' has not been observed under all possible environmental conditions. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Rosaceae.
*Botanical*.—*Rubus idaeus* L.
*Common name*.—Raspberry.
*Variety name*.—'DrisRaspFourteen'.

Parentage:

*Female parent*.—'RB629.4' (unpatented).
*Male parent*.—'Y454.3' (unpatented).

Plant:

*Height*.—201.2. cm.
*Width*.—133.2 cm.
*Length/width ratio*.—1.
*Growth habit*.—Semi-upright.
*Primocane* (*current year's cane*).—Cane length in autumn: 148.70 cm. Internodal distance at central ⅓ of cane: 7.50 cm. Primocane color: RHS 132B (Strong green).
*Very young shoot*.—Anthocyanin coloration of apex during rapid growth: Present.
*Floricane* (*previous year's cane*).—Dormant cane color: Purplish brown. Floricane color: RHS 177A (Moderate reddish brown). Fruiting lateral attitude: Horizontal to drooping.
*Prickles* (*spines*).—Length from base to tip at 1 in height at end of harvest: 0.52 mm. Color: Greenish brown.

Leaves:

*Predominant number of leaflets*.—Five.
*Profile of leaflets in cross section*.—Convex.
*Leaf arrangement*.—Compound-opposite.
*Color of upper surface*.—RHS 132C (Green).
*Color of lower surface*.—RHS 139B (Yellowish green).
*Leaf shape*.—Oblong.
*Shape of leaf base*.—Obtuse.
*Shape of leaf apex*.—Acuminate.
*Leaf margin*.—Serrate.
*Leaf texture*.—Rugose.
*Venation pattern*.—Pinnate.
*Vein color*.—RHS 135B (Moderate green).

*Terminal leaflet*.—Length: 138.7 mm. Width: 89.4 mm. Length/width ratio: 1.

*Lateral leaflets*.—Length (basal pair): 113.4 mm. Width (basal pair): 67.5 mm. Length/width ratio (basal pair): 1. Relative position of lateral leaflets: Free.

*Rachis length between terminal leaflet and adjacent lateral leaflets*.—38.8 mm.

*Petiole*.—Length: 72.2 mm. Diameter: 4 mm. Color: RHS 141C (Strong yellowish green).

Flowers:

*Length of inflorescence*.—80 mm.

*Diameter of flower*.—29.40 mm.

*Petal*.—Length: 9.08 mm. Width: 4.04 mm. Length/width ratio: 2. Color of upper surface: RHS NN155B (White). Color of lower surface: RHS NN155A (Yellowish white). Average number per flower: 7.1. Shape: Oblong.

*Sepal*.—Length: 9.08 mm. Width: 2.2 mm. Average number per flower: 5. Color: RHS N134D (Brilliant green).

*Pedicel*.—Length: 52.90 mm. Diameter: 1.09 mm. Color: RHS 141B (Strong yellowish green).

*Peduncle*.—Anthocyanin coloration: Present. Length: 14 mm. Diameter: 1.3 mm. Color: RHS 141A (Deep yellowish green).

Fruit:

*Length*.—24.70 mm.

*Diameter*.—22.80 mm.

*Length/width ratio*.—1.

*General shape in lateral view*.—Conical.

*Color*.—RHS 187A (Dark red).

*Average number of drupelets per berry*.—120.

*Average weight per berry*.—5.95 g.

*Market use of fruit*.—Fresh market.

Production:

*Main bearing type*.—Both on floricane (previous year's cane) in summer and on primocane (current year's cane) in autumn.

*Primocane* (*current year's cane*).—Time of month when beginning of flowering occurs: Mid-June. Time of month when beginning of fruit ripening occurs: Late June. Time interval for length of fruiting period: Mid-July to late October. Yield: 20,900 kg/ha to 38,900 kg/ha of fruit per season from 10-month-old plants when grown in Santa Cruz County, Calif.

*Floricane* (*previous year's cane*).—Time of month when bud burst occurs: Mid-April to late April. Time of month when beginning of flowering occurs: Late April. Time of month when beginning of fruit ripening occurs: Mid-May. Time interval for length of fruiting period: Mid-May to late July. Yield: 23,600 kg/ha to 45,600 kg/ha of fruit per season from 19-month-old plants when grown in Santa Cruz County, Calif.

COMPARISONS TO PARENTAL AND COMMERCIAL RASPBERRY VARIETIES

'DrisRaspfourteen' differs from the female parent raspberry variety 'RB629.4' (unpatented) in that fruit of 'DrisRaspFourteen' have better flavor and are lighter in color when compared with fruit of 'RB629.4'.

'DrisRaspFourteen' differs from the male parent raspberry variety 'Y454.3' (unpatented) in that fruit of 'DrisRaspFourteen' have better flavor and are larger in size when compared with fruit of 'Y454.3'.

'DrisRaspFourteen' differs from the commercial raspberry variety 'DrisRaspThirteen' (U.S. Plant Pat. No. 29,402) in that canes of 'DrisRaspfourteen' have sparse spines, whereas canes of 'DrisRaspThirteen' have medium spines. Moreover, leaflets of 'DrisRaspFourteen' have a convex profile in cross section, whereas leaflets of 'DrisRaspThirteen' have a concave profile in cross section. Further, terminal leaflets of 'DrisRaspFourteen' have a broad width, whereas terminal leaflets of 'DrisRaspThirteen' have a narrow width. In addition, peduncles of 'DrisRaspFourteen' have anthocyanin coloration present, whereas peduncles of 'DrisRaspThirteen' do not have anthocyanin coloration.

'DrisRaspFourteen' differs from the commercial raspberry variety 'DrisRaspEight' (U.S. Plant Pat. No. 27,644) in that very young shoots of 'DrisRaspFourteen' have anthocyanin coloration present on apex during rapid growth, whereas very young shoots of 'DrisRaspEight' do not have anthocyanin coloration on apex during rapid growth. Moreover, canes of 'DrisRaspFourteen' have sparse spines, whereas canes of 'DrisRaspEight' have medium spines. Further, leaflets of 'DrisRaspFourteen' have a convex profile in cross section, whereas leaflets of 'DrisRaspEight' have a concave profile in cross section. In addition, peduncles of 'DrisRaspFourteen' have anthocyanin coloration present, whereas peduncles of 'DrisRaspEight' do not have anthocyanin coloration.

What is claimed is:

1. A new and distinct variety of raspberry plant designated 'DrisRaspFourteen' as shown and described herein.

* * * * *